United States Patent [19]

Rieder

[11] Patent Number: 4,487,625

[45] Date of Patent: Dec. 11, 1984

[54] METHOD FOR INTERRUPTING BUD DORMANCY

[75] Inventor: Georg L. Rieder, Grobenzell, Fed. Rep. of Germany

[73] Assignee: SKW Trostberg, Fed. Rep. of Germany

[21] Appl. No.: 447,441

[22] Filed: Dec. 6, 1982

[30] Foreign Application Priority Data

Dec. 19, 1981 [DE] Fed. Rep. of Germany ....... 3150404

[51] Int. Cl.$^3$ ............................................. A01N 59/24
[52] U.S. Cl. ........................................ 71/77; 71/65; 71/118; 71/121
[58] Field of Search ...................... 71/121, 118, 77, 65

[56] References Cited

U.S. PATENT DOCUMENTS

| 2,314,091 | 3/1943 | Jones | 71/77 |
| 2,535,875 | 12/1950 | Stewart | 71/77 |
| 4,180,393 | 12/1979 | Aman | 71/65 |

FOREIGN PATENT DOCUMENTS

| 45-33079 | 10/1970 | Japan | 71/77 |
| 1265244 | 3/1972 | United Kingdom | 71/118 |
| 1542236 | 3/1979 | United Kingdom . | |

OTHER PUBLICATIONS

Iwasaki et al., I "Effects of Chilling, etc.," (1977), CA 88 No. 17163v, (1978).
Iwasaki et al., II "Effects of Bud Scale, etc.," (1980), CA 93 No. 180917f, (1980).
Inoue et al., "Control of Barnyard grass etc.," (1970), CA 74 No. 139734p, (1971).
Latzko et al., "Effect of Cyanamide, etc.," (1952), CA 47 p. 9423, (1953).
Imamaliev et al., "After Effect of Defoliants, etc.," (1969), CA 72 No. 99432p, (1970).
Shulman et al., "The Effect of Cyanamide, etc.," (1983) CA 98 No. 211502b, (1983).

*Primary Examiner*—Richard L. Raymond
*Attorney, Agent, or Firm*—Thomas L. Tully

[57] ABSTRACT

A method and a composition for interrupting bud dormancy of perennial crop-bearing plants, comprising a 0.1–10 weight percent, preferably a 1–3 weight percent aqueous cyanamide solution, which is applied to the plants and/or plant parts to be treated until they are completely wetted.

9 Claims, No Drawings

METHOD FOR INTERRUPTING BUD DORMANCY

BACKGROUND OF THE INVENTION

The growth and development of perennial crops follow a seasonal rhythm which is especially pronounced in moderate climates. At the end of a vegetation period, such plants cease growing after bearing fruit, and form buds. This budding enables a meristem, which has undifferentiated leaf and blossom structures, to survive under the unfavorable environmental conditions of winter since buds, in the latent stage, are much more resistant to frost and low temperatures than active tips of vegetation.

The duration of this latent stage, referred to as dormancy, is species-specific and depends upon environmental conditions, such as the temperature for example. This means the dormancy can only be terminated if the buds have been exposed to specific low temperatures for a certain length of time.

Bud dormancy, which occurs in all deciduous trees and bushes, is admittedly a natural regulation mechanism for survival of the plant species, but has several disadvantages for practical crop cultivation.

In ornamental plant cultivation, an effort is made to provide consumers with flowering plants not only during the natural vegetation period, but outside the usual flowering season as well; this is not easily possible because of bud dormancy, which terminates only after a certain period of cold has elapsed.

In grape and fruit growing, mild winters during which the necessary cold stimulus to interrupt dormancy is absent, can cause delayed as well as reduced bud break or development. The results of this delayed and inhomogeneous vegetative and generative development is a poor and inhomogeneous development of blossoms and fruit, which can produce markedly-reduced crop yields.

These problems are understandably of greater practical significance in those countries in which the necessary cold stimulus is absent, or occur with greater severity when crops or varieties must be cultivated which are not adapted to local conditions.

There has been no lack of efforts to control bud dormancy by artificial intervention. Thus, for example, nurseries have used artificial cold followed by heat treatment in climate-controlled rooms to cause lilacs or forsythia to bloom in December, for example. This method, known as "pushing" or "early pushing" (cf: U. Ruge: *Angewandte Pflanzenphysiologie;* Ulmer Verlag Stuttgart, 1966, pp. 70–79), also used for flower bulbs, is rather costly, since both the duration and intensity of the cold stimulus and the subsequent warm period and duration of illumination must be controlled precisely. In addition, this method is expensive because of high energy costs and naturally cannot be applied to field cultures such as grape and fruit growing.

Attempts have also been made to interrupt bud dormancy by using natural and synthetic growth substances (cf: H Jansen, *Wuchs and Hemmstoffe im Gartenbau;* Ulmer Verlag Stuttgart, 1969, pp. 63–68), although they are not yet in wide use. In addition, articles which have appeared in the *Journal of the American Society for Horticultural Science,* Vol. 102 (5), pp. 584–7, 1977 and the *Journal of Japanese Society for Horticultural Science,* Vol. 48 (4), pp. 395–8, 1980, have contained descriptions of a method of treating the dormant buds of grapevines with calcium cyanamide. Admittedly, an aqueous suspension of lime-nitrogen does produce a certain interruption of dormancy, but using aqueous suspensions is scarcely practical because these substances can be applied only with difficulty using conventional spraying equipment, and the calcium cyanamide suspension must, therefore, be applied to those parts of the plants to be treated, using a sponge or brush.

DESCRIPTION OF THE INVENTION

Therefore, the object of the present invention is to develop a means of interrupting bud dormancy, which does not suffer from the above-described disadvantages and which ensures uncomplicated handling.

This object is achieved according to the invention by virtue of the fact that an aqueous cyanamide solution with a content of 0.1–10 weight percent is used as a means for interrupting bud dormancy.

Surprisingly, it has been found that such a solution produces a bud-dormancy-interrupting effect. This was not expected because it was previously thought that a concentrated cyanamide solution, such as that used for defoliating grapevines in autumn, could have no effect on bud growth (cf: *Der Deutsche Weinbau,* Vol. 31 (26), 1976, p. 1058). It was, therefore, assumed that the observed effect of the calcium cyanamide suspension was attributable not to the cyanamide, but to the influence of the calcium ions and the finely-distributed carbon present in the calcium cyanamide. This is also consistent with the fact that calcium ions promote longitudinal growth and cell multiplication in meristematic tissue, such as that which is present in dormant buds (cf: K. Mengel, *Ernaehrung und Stoffwechsel der Pflanze;* VEB Gustav Fischer Verlag, Jena, 1965, p. 282). The action of the carbon is explained by the fact that the black coloration of the treated buds intensifies the absorption of light, and this temperature change influences bud dormancy.

The means according to the invention offer a simple and practical approach for interrupting bud dormancy, because it can be applied in a problem-free manner as an aqueous solution, using conventional spraying equipment. In addition to its ease of applicability, it also has the advantage of being suitable for field cultures, especially grapes and fruit. A content of 0.1–10 weight percent, preferably 1–3 weight percent, cyanamide is sufficient to achieve the desired effect. Wetting agents such as, for example, "Citowett" can also be used if desired. "Citowett" is a registered trademark for a nonionic alkylaryl polyglycol ether. In theory, such aqueous solutions are suitable for treating all kinds of plants, especially fruit trees and grapevines. Thus, for example, the aqueous cyanamide solution is applied to the grapevines at an appropriate concentration immediately after the conventional pruning of the vines in such a way that all of the existing resting buds are wetted by the solution in order to achieve an optimum effect. After only a few weeks, a definite difference is apparent between the grapevines treated with the cyanamide solution and the untreated vines, in terms of budding. The means according to the present invention causes earlier and much more profuse budding, which in turn produces earlier blossoming and advanced fruiting.

The following examples are intended to explain the invention in greater detail.

EXAMPLE 1

Grapevines of the Perlett variety (3rd year) are sprayed immediately after the pruning with a 2.5% aqueous cyanamide solution, using 600 liters of the aqueous solution per hectare (10,000 square meters). For evaluation, the number of buds and the number of growing buds were counted on forty branches after 15 to 32 days, and the averages determined:

|  | After 15 Days | | After 32 Days | |
| --- | --- | --- | --- | --- |
|  | No. of Buds | No. of Grwng Buds | No. of Buds | No. of Grwng Buds |
| Untreated | 117 | 0 | 114 | 15 |
| 2.5% cyanamide solution | 110 | 36 | 117 | 76 |

EXAMPLE 2

Grapevines of the Perlett variety were treated as in Example 1, covering the grapevines with plastic film in order to study the influence of temperature on the interruption of bud dormancy. Evaluation similarly to Example 1 produced the following values:

|  | After 15 Days | | After 32 Days | |
| --- | --- | --- | --- | --- |
|  | No. of Buds | No. of Grwng Buds | No. of Buds | No. of Grwng Buds |
| Untreated | 113 | 8 | 129 | 39 |
| 2.5% cyanamide solution | 111 | 92 | 120 | 103 |

EXAMPLE 3

Grapevines of the Thompson seedless variety were sprayed immediately after the pruning with a 2.5% aqueous cyanamide solution until run-off using a hand sprayer. One main branch on each of three grapevines was treated with the cyanamide solution and the second main branch was left untreated for comparison.

Budding began about two weeks earlier on the treated vines than on the untreated ones. After 57 days, 10 shoots were selected on each vine and the lengths of these shoots were measured:

|  | Treatment Shoot Length (average of 10 shoots) | | |
| --- | --- | --- | --- |
|  | Vine 1 | Vine 2 | Vine 3 |
| Untreated | 17.6 cm | 12.3 cm | 16.4 cm |
| 2.5% cyanamide solution | 25.5 cm | 26.4 cm | 33.4 cm |

EXAMPLE 4

Grapevines of the Thompson seedless variety were treated similarly to Example 3 with a 2.5% cyanamide solution to which a wetting agent was added. Evaluation of shoot length according to Example 3 as compared to untreated branches showed the following values:

|  | Treatment Shoot Length (average of 10 shoots) | | |
| --- | --- | --- | --- |
|  | Vine 1 | Vine 2 | Vine 3 |
| Untreated | 17.6 cm | 12.3 cm | 16.4 cm |
| 2.5% cyanamide solution + wetting agent | 28.6 cm | 29.5 cm | 34.3 cm |

The increase in shoot length also shows up clearly after treatment of apple, pear, and peach trees.

Variations and modifications of the present invention will be apparent to those skilled in the art within the scope of the present claims.

I claim:

1. Method for interrupting the bud dormancy of perennial crop-bearing plants after the plants bear fruit and cease growing and in the absence of a cold stimulus to interrupt dormancy, comprising the step of spraying such plants having existing resting buds with an aqueous cyanamide solution comprising from about 0.1% to about 10% by weight of dissolved cyanamide until the existing resting buds are wetted by said solution.

2. Method according to claim 1 in which the cyanamide solution comprises from about 1% to about 3% by weight of dissolved cyanamide.

3. Method according to claim 1 in which said cyanamide solution also comprises from about 0.1% to about 1% by weight of a wetting agent.

4. Method according to claim 2 in which said cyanamide solution also comprises from about 0.1% to about 1% by weight of a wetting agent.

5. Method according to claim 1 in which the cyanamide solution comprises about 2.5% by weight of dissolved cyanamide.

6. Method for interrupting the bud dormancy of perennial grapevine plants after the plants bear fruit and cease growing and in the absence of a cold stimulus to interrupt dormancy, comprising the step of spraying such plants having existing resting buds with an aqueous cyanamide solution comprising from about 1% to about 3% by weight of dissolved cyanamide until the existing resting buds are wetted by said solution.

7. Method according to claim 6 in which the cyanamide solution comprises about 2.5% by weight of dissolved cyanamide.

8. Method according to claim 6 in which said cyanamide solution also comprises from about 0.1% to about 1% by weight of a wetting agent.

9. Method according to claim 7 in which said cyanamide solution also comprises from about 0.1% to about 1% by weight of a wetting agent.

* * * * *